United States Patent
Rosenberg Nevo

(10) Patent No.: US 7,727,515 B2
(45) Date of Patent: Jun. 1, 2010

(54) DEODORANT COMPOSITIONS AND METHOD

(75) Inventor: Melvyn Rosenberg Nevo, Ramat-Gan (IL)

(73) Assignee: Assif - Science and Technology Projects Development Ltd., Ramat Gan (IL)

( * ) Notice: Subject to any disclaimer, the term of this patent is extended or adjusted under 35 U.S.C. 154(b) by 929 days.

(21) Appl. No.: 10/295,259

(22) Filed: Nov. 14, 2002

(65) Prior Publication Data
US 2003/0170190 A1   Sep. 11, 2003

Related U.S. Application Data

(63) Continuation of application No. 09/519,255, filed on Mar. 6, 2000, now abandoned.

(51) Int. Cl.
*A61K 8/00* (2006.01)
*A61K 8/18* (2006.01)
*A61Q 15/00* (2006.01)

(52) U.S. Cl. .......... 424/65; 424/401

(58) Field of Classification Search ............ 424/401, 424/65, 76.3
See application file for complete search history.

(56) References Cited

U.S. PATENT DOCUMENTS

| 3,708,435 | A | * | 1/1973 | Starkman | 132/200 |
| 4,675,178 | A | * | 6/1987 | Klein et al. | 424/65 |
| 5,720,949 | A | * | 2/1998 | Davis | 424/78.03 |
| 5,798,111 | A | * | 8/1998 | Kanga et al. | 424/401 |
| 5,928,631 | A | * | 7/1999 | Lucas et al. | 424/65 |
| 6,057,275 | A | * | 5/2000 | Fair et al. | 510/151 |
| 6,187,300 | B1 | * | 2/2001 | Motley et al. | 424/65 |
| 6,294,186 | B1 | * | 9/2001 | Beerse et al. | 424/405 |

OTHER PUBLICATIONS www.johnsonsbaby.com.*

* cited by examiner

*Primary Examiner*—Johann R Richter
*Assistant Examiner*—Danielle Sullivan
(74) *Attorney, Agent, or Firm*—Merchant & Gould P.C.

(57) ABSTRACT

A method for preventing the formation and/or for the removal of body odors, comprising priming the skin with a deodorant composition comprising an oil, for a period of time sufficient to allow binding of skin microorganisms and dissolution of odor into said composition, and thereafter washing off said composition with conventional detergents.

7 Claims, No Drawings

DEODORANT COMPOSITIONS AND METHOD

This application is a continuation of application Ser. No. 09/519,255, filed Mar. 6, 2000 now abandoned, which application(s) are incorporated herein by reference.

FIELD OF THE INVENTION

The present invention relates to deodorizing compositions. More particularly, the invention relates to a method for removing body odor and to deodorizing compositions for this purpose.

BACKGROUND OF THE INVENTION

Body odor is formed when fresh perspiration, which is odorless per se, is decomposed by microorganisms. This process takes place principally, though not solely, in the axilla, and a number of microorganisms are involved, each having different activity and leading to body odor of different strength and unpleasantness. The most prominent odor-producing microorganisms include aerobic diphtheroids, primarily *Corynebacterium* species and coagulase negative cocci such as Micrococcaceae.

The various microorganisms are found in different proportions in different individuals, and this is a reason for the fact that different individuals exhibit different body odors.

The commercial cosmetic deodorants are based on different active principles. The formation of perspiration is suppressed according to the known art by astringents, predominantly aluminum salts such as aluminum hydroxychloride. Apart from the denaturation of the skin proteins, however, the substances used for this purpose clog the pores, interfere drastically with the heat regulation of the axillary region, may cause cancer and other diseases, and should at best be used in exceptional cases. According to another accepted prior art method, the bacterial flora on the skin is reduced by antimicrobial substances. Ideally here, only the odor-causing microorganisms should be destroyed. In practice, however, it turns out that the non-odorous microflora of the skin, which may have a beneficial role, are damaged to the same extent. Finally, body odor can also be concealed by fragrances, which, however, is the least able to meet the aesthetic needs of the consumer, as the mixture of body odor and perfume fragrance smells rather unpleasant.

According to a recent patent on this subject (U.S. Pat. No. 5,318,778), deodorants should fulfill the following conditions:

1) The biological processes of the skin must not be impaired.

2) The deodorants should have no distinct intrinsic odor.

3) They must be harmless in the case of overdosage or other unintended use.

4) They should not concentrate on the skin after repeated use.

It should be possible to incorporate them easily into commercial cosmetic formulations.

Those which are known and usable are both liquid deodorants, for example aerosol sprays, roll-ons and the like and solid preparations, for example deodorant sticks, powders, powder sprays, intimate cleansers etc.

U.S. Pat. No. 5,318,778 approaches the problem by employing lantibiotics, which are said to be specific microbiocides which predominantly destroy odor-forming microorganisms.

All the prior art methods suffer from severe drawbacks: they require the masking of body odor which has already formed prior to the application of the deodorant, because the destruction of axillary microorganisms does not remove already formed odor. They require the use of antimicrobial agents which must inhibit the high microbial load and, quite importantly, they very often leave unpleasant stains or halos on the cloths, particularly at and around the axilla. Also the safety of many antiperspirants is dubious, due to the presence of potentially harmful components, and the result is often unpleasant.

It has now been surprisingly found, and this is an object of the invention, that it is possible to obviate all the aforesaid disadvantages of the prior art, in a simple and convenient way.

It is an object of the invention to provide a method for preventing and/or treating body odor, which is simple and convenient to use, and which does not leave a macroscopic residual layer on the skin.

It is another object of the invention to provide such a method, which does not lead to staining or haloing of clothing around the treated area.

It is yet another object of the invention to provide an antibody odor composition, which is convenient and easy to use, and which does not leave unpleasant left-over results, such as staining or haloing materials.

The invention is, of course, primarily concerned with the prevention of body odors in humans, more particularly where such body odor formation is the most pronounced, i.e., in the axilla. However, the invention is by no means limited to the use in the axilla, and any other body part requiring treatment can be treated according to the invention. Additionally, the invention is suitable for use in subjects other than humans, e.g., in house pets.

Other objects and advantages of the invention will become apparent as the description proceeds.

SUMMARY OF THE INVENTION

In one aspect, the invention is directed to a method for preventing the formation and/or for the removal of body odors, comprising bringing into contact with the area to be treated a stable skin deodorizing composition comprising an oil, for a period of time sufficient to allow dissolution of skin microorganisms and odor into said composition, thus priming the skin so that when the skin is subsequently washed with conventional detergents, the odors and microorganisms are removed.

In the context of the invention, the term "dissolution of skin microorganisms and odor" should be interpreted as meaning that microorganisms and odors which normally adhere to the skin interact with the oil-containing composition, so that they are efficiently washed off the skin upon subsequent rinsing with soap and water. The actual mechanism by which such microorganisms and odors are removed from the skin by this procedure, and the processes that the microorganisms undergo by the action of the oil component, are not a concern of the present invention. It is sufficient to say that such microorganisms and odors are not easily detached from the skin and, for instance, they are not effectively removed by water and soap. This is the reason why regular detergents which are not harmful to the skin cannot efficiently counter body odor. However, once the body-odor forming microorganisms and odors have been efficiently removed from the skin and washed away, their fate is not important, as the primary object of the invention has been achieved.

As stated, after the application of the composition of the invention, and after some time has been allowed for the microorganisms and odor to interact with said composition, and for the odor to solubilize into it, the composition can be washed away by conventional body detergents. This is conveniently done in the shower. Thus, little substantial residual materials are left on the skin—and there is less need to leave any such residual materials, since the effect of the invention, i.e., the removal of the microorganisms and odors has already been achieved.

The time needed for effectively priming the skin with the present compositions varies from one composition to the other, and will further vary from one person to the other. Each individual will easily determine the optimal time for an efficient and long-lasting treatment, but such times are generally in the range of 5 seconds to 5 minutes.

In another aspect, the invention is directed to a deodorizing composition comprising an oil as a skin priming agent for subsequent removal by rinsing with soap and water. The deodorizing composition can be provided in a variety of forms, e.g., as organic solutions and lotions. According to a preferred embodiment of the invention, the deodorizing composition of the invention is provided in the form of a solution and a stable water in oil or oil in water emulsion. The deodorizing composition according can further comprise additives, such as conventional deodorant components. While such additives are not essential to the invention, they may have collateral beneficial effects, such as residual scent, and their incorporation in the compositions of the invention is not deleterious to the invention. Such conventional deodorant components may comprise antibacterial and antiodor materials. Various different antibacterial and antiodor materials may be used in the invention. According to a preferred embodiment, however, the antibacterial material comprises benzalkonium chloride. As the compositions of the present invention do not remain in contact with the skin for long periods of time, the aforementioned antibacterial and antiodor materials may be used at concentrations higher than normally used in conventional deodorant preparations that remain on the skin for long periods of time. One such material Triclosan, may be used at concentrations of only 0.03 to 0.3% when used in conventional deodorants, but at higher levels (0.2 to 0.5%) when the composition is washed off (e.g. in the case of solid soap [Antiperspirants and Deodorants Ed. K Laden & C. Felger, 1988]). In the present invention, Benzalkonium chloride, for example, may be used at concentrations higher than 0.1% (w/v), a preferred range being 0.1% to 4.0% (w/v).

The oil to be used in the compositions of the invention may be any oil which primes the skin to enhance removal of bacteria and odors on subsequent soaping and washing. The skilled person will easily select suitable oils or oil combinations which give the desired results, by means of simple and straightforward tests. In principle, it is sufficient to rub the oil to be tested into the axilla of a subject. After waiting 3 minutes, the subject showers in the usual way, and an odor judge determines whether there has been a reduction in body odor, thus indicating whether the specific oil or oil combination is suitable for the intended purposes. Without wishing to limit the kind of oil employed in any way, it can be mentioned that illustrative and non-limitative examples of suitable oils include vegetable and synthetic oils, silicone based oils, isopropyl esters, hydrocarbons and their derivatives, or mixtures of two or more such oils. Suitable isopropyl esters are, for example, isopropyl myristate and isopropyl stearate.

Illustrative and non-limitative examples of suitable vegetal and animal oils include, e.g., sweet-almond oil, groundnut oil, wheatgerm oil, linseed oil, jojoba oil, apricot stone oil, walnut oil, palm oil, pistachio nut oil, sesame oil, rapeseed oil, cade oil, maize germ oil, peach stone oil, poppy seed oil, pine oil, castor oil, soya oil, avocado oil, safflower oil, coconut oil, hazelnut oil, olive oil, grapeseed oil, sunflower seed oil, whale oil, lard oil, horsehoof oil, tuna oil, caballine oil, otter oil, egg oil, sheep oil, seal oil, turtle oil, halibut liver oil, marmot oil, cod liver oil, neat's-foot oil and carbon oil. The oily phase can also contain a synthetic oil preferably consisting of carbon, hydrogen and oxygen, such as the glycol ethers or esters or glycerol ethers or esters described in French Patents No. 74/09,657, No. 75/24,656 and Nos. 75/24,657 and 75/24,658. The oily phase can also contain a mineral oil such as vaseline oil (liquid petrolatum), silicon oils or long-chain alcohols such as cetyl alcohol or stearyl alcohol.

When the composition of the invention is provided in the form of a stable emulsion, the emulsion may comprise water and/or a skin-compatible alcohol, and/or some water soluble components like propylene glycol, glycerol, thickeners, antibacterial materials etc. The final preparation can be in the form of a liquid, gel, cream, lotion, ointment or any other form suitable for body application.

Said emulsion can be a water-in-oil or an oil-in-water emulsion. Stable emulsions can be obtained using suitable conventional emulsifiers, such as sodium cetostearyl sulfate (Lanette E), polyoxyethylene cetyl/stearyl ether (Ceteareth-30) and polyoxyethylene laurylether (Dehydrol LS 3).

As stated, the composition of the invention is eventually almost entirely washed off the skin, although some small residue, which may remain on the skin, has no adverse effect. While this can be effected in any suitable way, it has been found that the deodorizing compositions according to the invention are particularly convenient for use as a pre-shower or in-shower deodorant. The invention is specifically intended to cover also pre-shower or in-shower deodorizing compositions comprising an oily phase.

The invention also encompasses a deodorizing kit comprising, in combination, any of the above-described deodorizing compositions, alongside a detergent. The detergent included in the kit may be in any convenient form, but preferably in the form of a solid or a liquid, or in the form of a gel or the like.

DETAILED DESCRIPTION OF PREFERRED EMBODIMENTS

The above and other characteristics and advantages of the invention will be more readily apparent through the following detailed description of preferred embodiments thereof.

EXAMPLE 1

The assay of the antimicrobial activities of the various formulations was used as a rapid, primary screening method for identifying those formulations that are potentially useful as deodorants. Antimicrobial activity was tested by applying samples (5 µl) of the formulations (listed in Table I) onto lawns of axillary and other bacteria. (The liquid was applied directly to the agar.) Each active material of Table I was formulated in isopropyl myristate, at the concentration (% w/w) given in that table.

The effect of the formulations on microbial growth is shown in Table I below. In the table, "+" indicates full growth inhibition (transparent zone), "−" indicates lack of inhibition, and "+/−" indicates partial inhibition (translucent zone). The values (in centimeters) indicate the diameter of the inhibition zone.

The abbreviations used herein are as follows:
TAGAT: polyoxyethylene hydrogenated castor oil
IRGASAN: trichlorohydroxydiphenyl ether

TABLE I

| PS Form No. | ACTIVE COMPONENTS | Bacillus | S. epidermidis | S. aureus | C. xerosis | Micrococcus luteus | Serratia marcescens |
|---|---|---|---|---|---|---|---|
| 1 | 1% Benzalkanium chloride (preventol 80 Bayer, Germany) | +,1.2 cm | +,1.8 cm | +,1.2 cm | +,1.6 cm | +,2.2 cm | +/− |
| 2 | 0.89% cremogen henna neutral* | +,0.3 cm | +/−,0.3 cm | — | +,0.5 cm | +,1.3 cm | — |
| 3 | 0.85% preventol 80 + 0.85% cremogen henna neutral* | +,2.0 cm | +,3.0 cm | +,2.0 cm | +,2.2 cm | +,2.6 cm | +,0.9 cm |
| 4 | 1% pine oil | — | — | — | — | — | — |
| 5 | 1% orange terpenes | — | +/−,0.3 cm | — | +/−0.3 cm | +/− | — |
| 6 | 0.3% IRGASAN | — | +,1.6 cm | +,2.0 cm | +,1.3 cm | +,1.5 cm | — |
| 7 | 1% black henna AMI** | +,0.3 cm | +/−,0.4 cm | +,0.4 cm | +,0.5 cm | +,0.4 cm | — |
| 8 | 1% preventol 80 + 1% black henna* AMI** | +,2.4 cm | +,2.6 cm | +,2.6 cm | +,2.4 cm | +,3.2 cm | +,0.6 cm |
| 9 | 1% preventol 80 + 1% black henna AMI** + 1% orange terpenes | +,2.4 cm | +,2.6 cm | +,2.2 cm | +/−,2.2 cm | +,4.0 cm | +,0.9 cm |
| 10 | 2% (black henna AMI**) | — | — | +/− | +/−,0.8 cm | +,2.0 cm | +/− |
| 11 | 1% Bio-Botanica-FE, Neutral henna | — | — | +/− | +,0.5 cm | +,1.0 cm | +/− |
| 12 | 0.75% Vege-Tech Henna, neutral U.S.A. | +,0.7 cm | +,0.5 cm | ++/−,0.3 cm | +,0.8 cm | +,0.7 cm | +,0.5 cm |
| 13 | 0.85% preventol 80 + 0.85% Vege-Tech Henna, neutral U.S.A. | +,1.3 cm | +,2.2 cm | +,1.8 cm | +,2.6 cm | +,2.8 cm | +,1 cm |

*Haarmann & Reimer, Germany
**Alban Muller International, France.

EXAMPLE 2

A group of ten individuals performed the following experiment. Prior to evening shower, the individuals rubbed their right armpits with formulation Pre-shower 3, and their left armpits with placebo (compositions given below). After waiting for three minutes the subjects showered as usual. Microbial counts were estimated directly before application, and the following morning. The individuals themselves, as well as independent judges scored the armpit odors and recorded them, before and after treatment.

| Compositions | wt % |
|---|---|
| 1. Pre-shower 3 | |
| Isopropyl myristate | 90 |
| Preventol 80 | 1 |
| Ethanol | 8 |
| Perfume (Italy) | 1 |
| 2. Placebo | |
| Water | 90.5 |
| TAGAT | 1 |
| Perfume | 0.5 |
| Ethanol | 8 |

The results showed a reduction of 1.5-2 orders of magnitude in bacterial counts in the experimental (right armpit), as compared to no reduction in the control (left armpit).

Similar reductions were observed by the participants in scoring the odor from the armpits, i.e., that the experimental armpit was free or almost free of odor the morning following application, whereas the control armpit had substantial odor. The results show that this invention is highly effective in long-lasting (ca. 8 hours) reduction of microbial counts and odor levels.

EXAMPLE 3

Operating essentially as in Example 2, groups of volunteers tested the following solutions and emulsions:

| | wt % |
|---|---|
| Composition A | |
| Isopropyl myristate | 99 |
| Perfume | 1 |
| Composition B | |
| Isopropylstearate | 80 |
| Olive oil | 20 |

-continued

| | wt % |
|---|---|
| Composition C | |
| Isopropyl palmitate | 70 |
| Paraffin oil | 27 |
| Tween 80 | 2 |
| Perfume | 1 |
| Composition D | |
| Octyl palmitate | 90 |
| Ethyl alcohol | 5 |
| Isopropanol | 3 |
| Benzalkonium chloride | 2 |
| Composition E | |
| Isopropyl myristate | 95 |
| Silica (Aerosil 200) | 3 |
| Benzalkonium chloride | 1 |
| Perfume | 1 |
| Composition F | |
| Isopropyl stearate | 93 |
| Stearalkonium hectorite | 5 |
| Benzalkonium chloride | 1 |
| Perfume | 1 |
| Composition G | |
| Mineral oil | 90 |
| Glyceryl behenate | 8 |
| Cetylpyridinium chloride | 1 |
| Perfume | 1 |
| Composition H | |
| Isopropyl stearate | 20 |
| Stearyl alcohol | 10 |
| Ceteareth-30 | 3 |
| Benzalkonium chloride | 1 |
| Water | 65 |
| Perfume | 1 |
| Composition I | |
| Isopropyl myristate | 15 |
| Ceteareth-20 | 5 |
| Cetyl alcohol | 8 |
| Benzalkonium chloride | 1 |
| Perfume | 1 |
| Water | 70 |
| Composition J | |
| Isopropyl stearate | 80 |
| sesame oil | 18 |
| cetrimonium chloride | 1 |
| cetylpyridinium chloride | 0.8 |
| Perfume | 0.2 |
| Composition K | |
| White mineral oil | 80 |
| n-octanol | 10 |
| ethyl alcohol | 6 |
| aq. henna extract | 3 |
| cetylpyridinium chloride | 0.8 |
| Perfume | 0.2 |
| Composition L (Cream) | |
| Isopropyl myristate | 83.5 |
| Compritol 888 ATO | 15 |
| Preventol R80 | 1 |
| Perfume | 0.5 |
| Composition M (Gel) | |
| Isopropyl myristate | 90.5 |
| Preventol 80 | 1 |
| Perfume | 0.5 |
| Aerosil A200 | 8 |
| Composition N (Conditioner) | |
| Isopropyl myristate | 15/20 |
| Lanette O | 10 |

-continued

| | wt % |
|---|---|
| Emulgin B2 | 5 |
| Preventol 80 | 1 |
| Perfume | 0.5 |
| Water | 68.5/63.5 |

The results showed that all of these formulations were effective in reducing axillary odor and bacterial levels.

EXAMPLE 4

Each of the subjects in a group of 75 volunteers were randomly assigned to one of two groups. In one group, the subjects applied Pre-shower 3 of Example 2 to the right armpit, and placebo to the left armpit; the second group vice versa. The compositions of these formulations are given in Example 2 above.

After application of the above formulations, the following assessments were made:
 a. axillary odor was scored by a panel of three odor judges;
 b. axillary odor was scored by the subjects themselves; and
 c. axillae were sampled for bacterial counts.

The statistical significance of the results was assessed by application of Student's paired t-test. Baseline measurements were taken late in the afternoon on day 1. The same night, subjects applied the samples to their axillae and then showered in the normal way, followed by self-assessment of axillary odor. In the morning of day 2, the self-assessment of axillary odor was repeated, and samples for bacterial counts taken. Following this, the subjects showered and, again, performed self-assessment of odor. Late in the afternoon of day 2, subjects were scored for axillary odor by the panel of odor judges, self-assessment was repeated, and axillary bacterial levels sampled.

The results show that according to all three assessment methods, the pre-shower treatment was highly effective ($p<0.001$) as compared with placebo.

All the above description and examples have been given for the purpose of illustration and are not intended to limit the invention in any way. Many modifications can be made in the compositions of the invention. For instance, different oily phases or combinations of two or more such oily phases can be used, many different additives can be incorporated in the compositions of the invention, be they antibacterially active or not, and many different aqueous or organic non-oleous phases can be added, to provide solutions, lotions, emulsions, gels, etc., all without exceeding the scope of the invention.

The invention claimed is:

1. A method of removing body odors, the method comprising the steps of:
 (a) priming the skin by applying a deodorizing composition to the axilla region of a human, the deodorizing composition being in the form of an emulsion, the deodorizing composition comprising a first component including an oil selected from the group consisting of vegetable oils, animal oils, synthetic oils, silicone based oils, isopropyl esters, hydrocarbons, and mixtures thereof, wherein the synthetic oils consist of carbon, hydrogen, and oxygen, and a second component including at least one of an antibacterial material and an antiodor material for a time period of from about 5 seconds to about 5 minutes; and
 (b) removing the deodorizing composition after the time period with a detergent.

2. A method according to claim 1, wherein the emulsion comprises water.

3. A method according to claim 1, wherein the antibacterial material comprises benzalkonium chloride.

4. A method according to claim 3, wherein the benzalkonium chloride is at concentrations of about 0.1% (w/v) or higher.

5. A method according to claim 4, wherein the benzalkonium chloride is at a concentration in the range of about 0.1% to 4.0% (w/v).

6. A method according to claim 1, wherein the step of priming the skin comprises applying a deodorizing composition comprising an oil selected from the group consisting essentially of sweet-almond oil, groundnut oil, wheatgerm oil, linseed oil, jojoba oil, apricot stone oil, walnut oil, palm oil, pistachio nut oil, sesame oil, rapeseed oil, cade oil, maize germ oil, peach stone oil, poppy seed oil, pine oil, castor oil, soya oil, avocado oil, safflower oil, coconut oil, hazelnut oil, olive oil, grapeseed oil, sunflower seed oil, whale oil, lard oil, horsehoof oil, tuna oil, caballine oil, otter oil, egg oil, sheep oil, seal oil, turtle oil, halibut liver oil, marmot oil, cod liver oil, neat's-foot oil, and carbon oil.

7. A method of removing body odors, the method comprising the steps of:
   (a) priming the skin by applying a deodorizing composition to the axilla region of a human for a time period of from about 5 seconds to about 5 minutes, the deodorizing composition comprising a first component including an isopropyl ester, and a second component including at least one of an antibacterial material and an antiodor material; and
   (b) removing the deodorizing composition after the time period with a detergent.

* * * * *